US00PP28991P3

(12) United States Plant Patent
Kordes

(10) Patent No.: US PP28,991 P3
(45) Date of Patent: Feb. 27, 2018

(54) GRANDIFLORA ROSE PLANT NAMED 'KORMARZAU'

(50) Latin Name: *Rosa hybrida*
Varietal Denomination: KORmarzau

(71) Applicant: W. Kordes Söhne Rosenschulen GmbH & Co. KG, Klein Offenseth-Sparrieshoop (DE)

(72) Inventor: Tim-Hermann Kordes, Klein Offenseth-Sparrieshoop (DE)

(73) Assignee: W. Kordes Söhne Rosenschulen GmbH & Co. KG, Offenseth-Sparrieshoop (DE)

( * ) Notice: Subject to any disclaimer, the term of this patent is extended or adjusted under 35 U.S.C. 154(b) by 40 days.

(21) Appl. No.: 14/999,872

(22) Filed: Jul. 13, 2016

(65) Prior Publication Data

US 2018/0020581 P1 Jan. 18, 2018

(51) Int. Cl.
*A01H 5/02* (2006.01)

(52) U.S. Cl.
USPC ..... Plt./137

(58) Field of Classification Search
USPC ..... Plt./137
See application file for complete search history.

*Primary Examiner* — Keith O Robinson
(74) *Attorney, Agent, or Firm* — Samuel R. McCoy, Jr.

(57) ABSTRACT

'KORmarzau' is a new and distinct variety of *Rosa hybrida* which is characterized by the combination of a compact and bushy growth habit, a moderately vigorous rate of growth, excellent resistance to common rose diseases, and panicles bearing one to six very double cream pink flowers. The new variety propagates successfully by stem cuttings and grafting and has shown to be uniform and stable in the resulting generations from asexual propagation.

1 Drawing Sheet

Latin name of genus and species: The Latin name of the genus and species of the novel variety disclosed herein is *Rosa hybrida*.

Variety denomination: The inventive variety of *Rosa hybrida* disclosed herein has been given the variety denomination 'KORmarzau'.

STATEMENT REGARDING PRIOR DISCLOSURES BY THE INVENTOR UNDER 37 C.F.R. 1.77(B)(6)

The first public disclosure of the claimed plant was made on Jul. 15, 2015 at a public ceremony where cut stems of the claimed plant were displayed by the inventor. 'KORmarzau' was not publically available or sold prior to one year before the date of the instant application.

BACKGROUND OF THE INVENTION

Parentage: The *Rosa hybrida* variety 'KORmarzau' is the result of a controlled cross-pollination breeding program carried out by the inventor in Klein Offenseth-Sparrieshoop, Germany. The objective of the said breeding program was to create a new and distinct rose plant with unique qualities, such as:

1. Uniform growth and flowering; and
2. Abundant, recurrent cream pink flowers; and
3. Attractive and abundant foliage; and
4. Resistance to diseases encountered in landscapes and gardens.

This combination of qualities is not present in prior rose cultivars known to the inventor. These objectives have been substantially achieved and in that distinguish 'KORmarzau' from all other varieties known to the inventor.

'KORmarzau' is a seedling selection which resulted from the controlled pollination of an unnamed *Rosa hybrida* seedling developed and owned by the same inventor, the seed parent, and *Rosa hybrida* 'NOAgut' (unpatented), the pollen parent, during the summer of 2003. As part of a rose development program, Tim-Hermann Kordes germinated seeds from the aforementioned hybridization during the following winter and conducted evaluations and observations on the resulting seedlings in a controlled environment in Klein Offenseth-Sparrieshoop, Germany. The resulting seedlings exhibited distinctive physical and biological characteristics. The new rose plant was selected as a single plant in May of 2004 from the seedling beds due to its superior characteristics and asexually propagated for further evaluation. This new and distinctive rose variety was given the name 'KORmarzau'.

Asexual Reproduction: 'KORmarzau' was first asexually propagated by bud grafting in July of 2004 at the inventor's nursery in Klein Offenseth-Sparrieshoop, Germany. Subsequently, 'KORmarzau' has been successfully propagated by stem cuttings and bud grafting in Jackson County, Oreg. These initial and other subsequent propagations conducted in controlled environments demonstrate that 'KORmarzau' reproduces true to type in successive generations of asexual reproduction.

SUMMARY OF THE INVENTION

The following characteristics have been repeatedly observed and represent the distinguishing characteristics of the new *Rosa hybrida* cultivar 'KORmarzau'. These traits, in combination, distinguish 'KORmarzau' as a new and distinct cultivar.

1. *Rosa hybrida* 'KORmarzau' exhibits a moderately vigorous growth rate; and
2. *Rosa hybrida* 'KORmarzau' exhibits a compact, upright and bushy growth habit; and
3. *Rosa hybrida* 'KORmarzau' exhibits excellent resistance to rust, black spot disease, *Botrytis* and powdery mildew; and
4. *Rosa hybrida* 'KORmarzau' exhibits panicles of 1 to 6 cream pink flowers held slightly pendant; and
5. *Rosa hybrida* 'KORmarzau' exhibits very double flowers of large size for a grandiflora rose.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORmarzau', taken from a two year old plant.

DETAILED BOTANICAL DESCRIPTION

The following is a detailed botanical description of a new and distinct variety of *Rosa hybrida* known as 'KORmarzau', based upon observations made in May of 2016 from two year old, field-grown plants in Jackson County, Oreg. Those skilled in the art will appreciate that certain characteristics will vary with older or, conversely, with younger plants. 'KORmarzau' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2001 edition except where common terms of color are used.

A botanical description of 'KORmarzau' and comparisons with the parents and closest known comparator variety of *Rosa hybrida* are provided below.

General plant description:

*Growth rate*.—Moderately vigorous.

*Growth habit*.—Compact, bushy.

*Mature dimensions*.—90 cm tall and 70 cm wide, on average.

*Cold hardiness*.—Grown successfully in USDA Hardiness Zones 5.

*Propagation*.—Stem cuttings and bud grafting.

*Disease resistance*.—Excellent resistance to powdery mildew (*Sphaerotheca pannosa*), blackspot (*Diplocarpon rosae*), rust (*Phragmidium* sp.) and *Botrytis* diseases under normal growing conditions in Jackson County, Oreg.

Root system:

*Type*.—Fibrous root system.

*Branching*.—Freely branched.

*Density*.—Moderately dense.

*Distribution*.—Roots deep into the soil profile.

Stems:

*Stem color*.—Young stems are Yellow-Green Group 146B; mature stems are Yellow-Green Group 146A.

*Anthocyanin intonations*.—Intonations of Greyed-Purple Group 185B are strongest in full sun exposure.

*Stem surface texture*.—Both juvenile and mature stems are smooth.

*Stem dimensions*.—Typical mature stems are approximately 60 cm long and 5 mm in diameter.

*Prickles*.—Incidence — Typically 9 prickles per 10 cm of stem, on average. Size — Average length is 8 mm long. Immature prickle color — Greyed-Orange Group 164B. Mature prickle color — Yellow-Green Group 147C, with anthocyanin intonations of Greyed-Purple Group 185B. Shape — Concave. Texture — Smooth.

Leaves:

*Arrangement*.—Imparipinnate compound leaves; mature axillary leaves consisting of 5 leaflets.

*Attachment*.—Petiolate.

*Dimensions*.—180 mm long and 120 mm wide.

*Abundance*.—Very abundant; approximately 100 leaves.

*Stipules*.—Size — 25 mm long and 18 mm wide. Stipule color — Yellow-Green Group 146B. Anthocyanin intonations — Greyed-Purple Group 183B intonations are present on the abaxial surface; intonations are also present at and near the midrib of the adaxial surface. Stipitate glands — A limited number of stipitate glands are present on the margins; a few stipitate glands are present on the abaxial leaf surface. Margins — Serrulate, with stipitate glands. Texture, adaxial surfaces — Glabrous. Texture, abaxial surfaces — Glabrous. Apex — Apiculate. Base — Fused to the petiole.

*Petiole*.—Length — Average 30 mm. Diameter — Average 3.0 mm. Petiole color, adaxial surface — Yellow-Green Group 146B. Petiole color, abaxial surface — Yellow-Green Group 146C. Anthocyanin intonations — Greyed-Purple Group 183B intonations are present on and near the midrib of adaxial surface; light intonations are present on the abaxial surface. Margins — Few stipitate glands. Prickles — A single prickle is present approximately midway along the petiole. Stipitate glands — A limited number of stipitate glands are present on the margins and the abaxial surface. Texture — Glabrous. Strength — Strong.

*Rachis*.—Length — Average 30 mm. Diameter — Average 2.0 to 3.0 mm. Color — Yellow-Green Group 146C. Anthocyanin intonations — Intonations of Greyed-Red Group 183A are present on the adaxial surface. Margins — With very few stipitate glands. Prickles — A few small prickles on the abaxial surface. Stipitate glands — A limited number of stipitate glands are present. Texture — Glabrous.

*Leaflets*.—Dimensions — Average size of the terminal leaflet is 75 mm long and 55 mm wide. Shape — Ovate. Apex — Mucronate. Base — Obtuse. Margins — Serrulate; not undulated. Luster, texture and pubescence; adaxial surface — Semi-glossy, smooth and glabrous. Luster, texture and pubescence; abaxial surface — Matte, smooth and glabrous. Juvenile foliage color, adaxial surface — Yellow-Green Group 146A. Juvenile foliage color, abaxial surface — Yellow-Green Group 146B. Mature foliage color, adaxial surface — Yellow-Green Group 147A. Mature foliage color, abaxial surface — Yellow-Green Group 147C. Anthocyanin intonations — Intonations of Greyed-Purple Group 183A are present on both surfaces of the juvenile foliage. Venation — Reticulate. Petiolule — Dimensions — 2.0 mm long and 0.5 mm in diameter. Petiolule color, adaxial surface — Greyed-Purple Group 183A. Petiolule color, abaxial surface — Yellow-Green Group 147C. Anthocyanin intonations — Intonations of Greyed-Purple Group 183C are present on the abaxial surface. Prickles — None present. Texture, adaxial and abaxial surfaces — Leathery.

Inflorescence:

*Inflorescence type*.—Panicles which bear 1 to 6 flower buds. Flowers are held slightly pendant.

*Blooming habit*.—Recurrent; floriferous.

*Size*.—14 cm tall and 15 cm wide, on average.

*Peduncle*.—Length — 60 to 90 mm average length. Diameter — 3.0 to 4.0 mm average diameter. Color — Yellow-Green Group 146C. Anthocyanin intonations — Intonations of Greyed-Purple Group 183C. Strength — Strong. Surface — Smooth; glabrous.

Flowering laterals: Present below the initiation of inflorescence. Generally 1 to 2 flowering laterals are present, with 1 to 2 flowers per flowering shoot.

Bud:

*Bud form*.—Short; globular.

*Size*.—Upon opening, 40 mm in length from base of receptacle to distal end of bud and 35 mm diameter at its widest point.

*Texture*.—Smooth.

*Color, as sepals first unfold*.—Red Group 48C.

*Color when one-quarter open, inner side*.—Marginal zone — Red Group 48C. Middle zone — Red Group 49C. Basal zone — Red Group 37D.

*Color when one-quarter open, outer side*.—Marginal zone — Red Group 48C. Middle zone — Red Group 49C. Basal zone — Red Group 48B to 48D.

Flower:

*Pedicel*.—Length — 60 to 120 mm average length. Diameter — 4.0 to 5.0 mm average diameter. Color — Yellow-Green Group 146C. Anthocyanin intonations — Very strong intonations of Greyed-Red Group 182A to 182C. Strength — Strong. Surface — Smooth; glabrous.

*Calyx*.—General — Comprised of five polysepalous sepals, with weak foliaceous appendages present on three sepals. Diameter of calyx — 75 mm, at anthesis. Sepals — Color, upper surface — Yellow-Green Group 146D. Color, lower surface — Yellow-Green Group 146C. Anthocyanin intonations — Intonations of Greyed-Purple Group 184B on the central area of the outer surface. Size — 20 mm long and 15 mm wide, on average. Apex — Typically, three sepals are cirrose and two sepals apiculate. Base — Flat at union with receptacle. Quantity — Five. Upper surface — Strongly pubescent. Lower surface — Lightly pubescent, with moderate stipitate glands. Margins — Strongly pubescent.

*Corolla*.—Habit — Very double. General shape of corolla — Cup-open; rosette. Shape of corolla when viewed from the side — Upon opening, upper portion — Flat. Upon opening, lower portion — Concave. Open flower, upper portion — Flat. Open flower, lower portion — Concave. Dimensions — Large size for a grandiflora rose. When open, the average flower diameter is 90 mm and the average flower height is 55 to 60 mm. Fragrance — Moderate fragrance. Duration — On the plant for 3 to 7 days; 4 to 6 days as a cut flower. Senesced petals drop away cleanly. Petals — Petal count — Exhibits very double flowers with an average of 120 petals under normal conditions. Petal reflex — Petals are somewhat reflexed. Timing of petal reflex — Simultaneous. Petal margin — Entire. Petal shape — Obovate. Apex — Obtuse. Base — Inner petals are attenuate; outer petals are obtuse. Dimensions — 40 to 50 mm long and 15 to 50 mm wide. Texture, inner surface — Smooth. Texture, outer surface — Smooth. Petal color, upon opening — Outermost petals, inner surface — Red Group 49D. Outermost petals, outer surface — Red Group 49D. Innermost petals, inner surface — Red Group 38C. Innermost petals, outer surface — Red Group 38C. Basal petal spots, upon opening — Outermost petals — Color, inner surface — Yellow Group 2B. Color, outer surface — Green-Yellow Group 1B. Dimensions — 10 mm wide and 10 mm tall. Innermost petals — Color, inner surface — Yellow Group 6A. Color, outer surface — Green-Yellow Group 1C. Dimensions — 10 mm wide and 10 mm tall. Petal color, after opening — Outermost petals, inner surface — White Group N155B. Outermost petals, outer surface — White Group N155C. Innermost petals, inner surface — Red Group 56C. Innermost petals, outer surface — Red Group 56D. Basal petal spots, after opening — Outermost petals — Color, inner surface — Yellow Group 2D. Color, outer surface — Yellow Group 2D. Dimensions — 10 mm wide and 8mm tall. Innermost petals — Color, inner surface — Yellow Group 2C. Color, outer surface — Yellow Group 2C. Dimensions — 2 mm wide and 10 mm tall. General Tonality — On open flower, Red Group 49C to 49D. No change in general tonality at the end of the fifth day; thereafter the general tonality is Red Group 56D. Petaloids — Quantity — 30 petaloids per flower, on average. Dimensions — Variable; approximately 15 to 25 mm long and 5 to 10 mm wide. Color, inner surface — Red Group 56B to 56D. Color, outer surface — Varied from White Group N155C to Red Group 56D. Margins — Entire and undulated. Shape — Obovate to spatulate. Apex — Obtuse. Base — Attenuate. Texture, inner and outer surfaces — Smooth.

Reproductive organs:

*Stamens*.—Quantity — Approximately 40, on average, arranged around the styles. Anthers — Shape — Reniform. Dimensions — 4.0 mm long and 1.0 mm wide, on average. Color — Greyed-Yellow Group 160B. Pollen — Present; abundant. Color is Greyed-Orange Group 163B. Filaments — Color — Yellow Group 3A, with intonations of Red Group 48B. Length — 10 to 12 mm.

*Pistils*.—Quantity — Average; approximately 30. Stigmas — Size — 2.0 mm. Location — Inferior in position to anthers. Color — Yellow Group 11A. Styles — Length — Approximately 8.0 mm long. Color — Yellow-Green 145C, with intonations of Red Group 53C.

*Ovary*.—Dimensions — 8 mm long and 10 mm in diameter. Color — White Group 155B.

*Receptacle*.—Shape — Funnel-shaped. Dimensions — Approximately 15 mm high and 18 mm wide. Color — Yellow-Green Group 146D. Texture — Smooth; glabrous.

Hips and seed formation: Not observed.

COMPARISONS WITH THE PARENTS

The new rose plant may be distinguished from its seed parent, an unnamed *Rosa hybrida* seedling, by the following combination of characteristics:

1. 'KORmarzau' exhibits cream pink flowers, whereas the seed parent exhibits deep pink flowers.
2. 'KORmarzau' exhibits a very double petal count, whereas the seed parent exhibits a semi-double petal count.
3. 'KORmarzau' exhibits moderate fragrance, whereas the seed parent exhibits intense fragrance.

The new rose plant may be distinguished from its pollen parent, *Rosa hybrida* 'NOAgut', by the following combination of characteristics:

1. 'KORmarzau' exhibits cream pink flowers, whereas 'NOAgut' exhibits salmon red flowers.
2. 'KORmarzau' exhibits a very double petal count, whereas 'NOAgut' exhibits a double petal count.
3. 'KORmarzau' exhibits inflorescences which bear one to six flowers, whereas the flowers of 'NOAgut' are solitary.

COMPARISON WITH THE MOST SIMILAR *ROSA* CULTIVAR KNOWN TO THE INVENTOR

For a comparison, several physical characteristics of the *Rosa hybrida* variety 'KORtekcho', a rose variety from the same inventor which is described and illustrated in U.S. Plant Patent No. 25,993, are compared to 'KORmarzau' in Chart 1.

CHART 1

| Characteristic | 'KORmarzau' | 'KORtekcho' |
|---|---|---|
| Bud form. | Globular. | Pointed ovoid. |
| Petal count. | 120. | 75. |
| Fragrance. | Moderate. | Strong. |

That which is claimed:

1. A new and distinct variety of rose plant named 'KORmarzau', as described and illustrated herein.

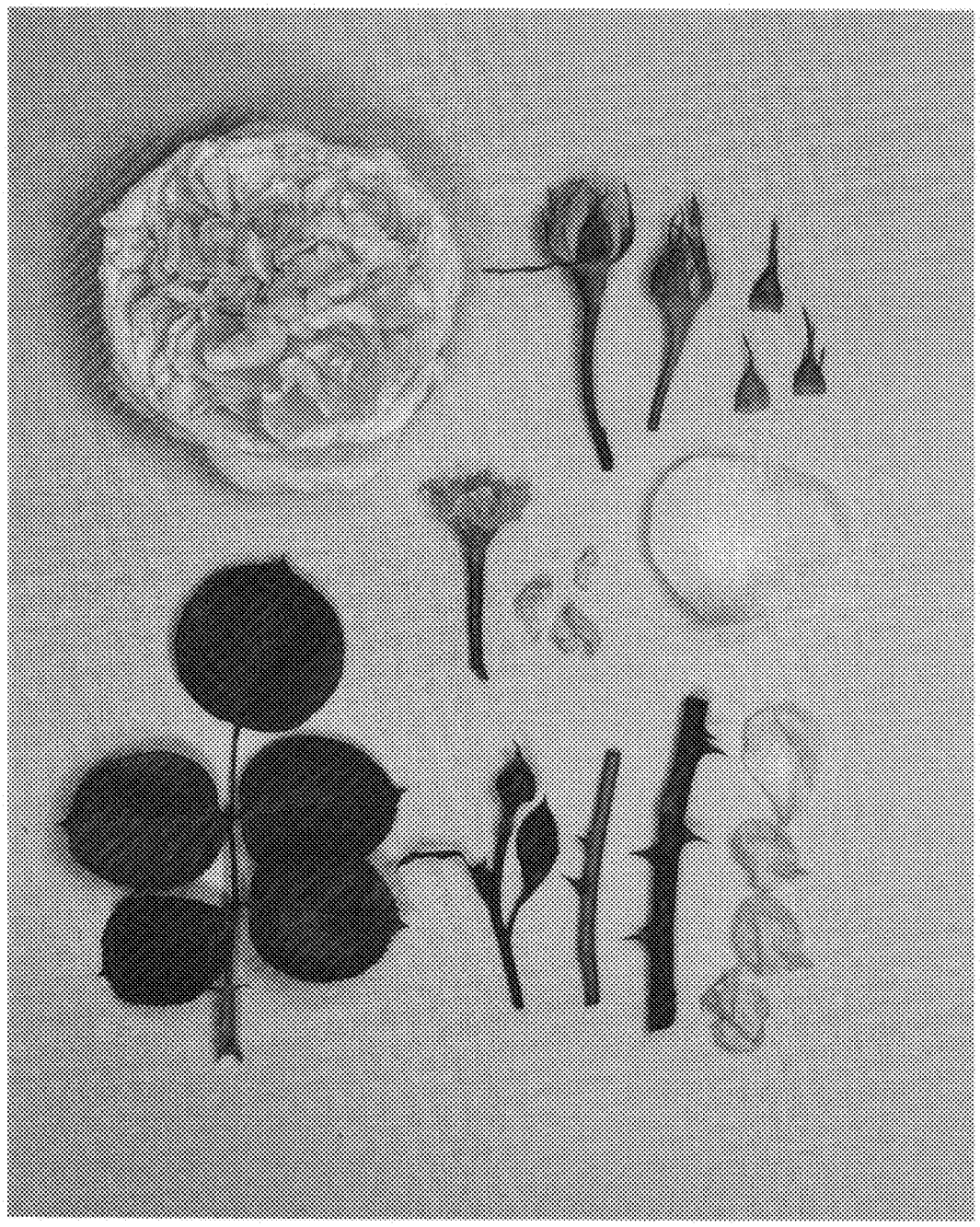

* * * * *